(12) United States Patent
Jang et al.

(10) Patent No.: US 10,080,485 B2
(45) Date of Patent: Sep. 25, 2018

(54) ENDOSCOPE

(71) Applicant: GWANGJU INSTITUTE OF SCIENCE AND TECHNOLOGY, Gwangju (KR)

(72) Inventors: Hwanchol Jang, Gwangju (KR); Heung-No Lee, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 137 days.

(21) Appl. No.: 15/166,276

(22) Filed: May 27, 2016

(65) Prior Publication Data

US 2016/0345813 A1    Dec. 1, 2016

(30) Foreign Application Priority Data

May 28, 2015 (KR) .......................... 10-2015-0075285

(51) Int. Cl.
*A61B 1/07* (2006.01)
*H04N 5/225* (2006.01)
(Continued)

(52) U.S. Cl.
CPC ............ *A61B 1/07* (2013.01); *A61B 1/00009* (2013.01); *A61B 1/042* (2013.01); *A61B 1/063* (2013.01);
(Continued)

(58) Field of Classification Search
CPC .................................. A61B 1/07; G02B 21/06
See application file for complete search history.

(56) References Cited

U.S. PATENT DOCUMENTS

| 4,273,419 A * | 6/1981 | Geary ................. G01N 21/255 356/432 |
| 6,927,859 B2 * | 8/2005 | Kwok ............... G01N 21/5911 250/559.02 |

(Continued)

FOREIGN PATENT DOCUMENTS

KR         101423964 B1        7/2014

OTHER PUBLICATIONS

Michal Aharon et al., "K-SVD: An Algorithm for Designing Overcomplete Dictionaries for Sparse Representation", IEEE Transactions on Signal Processing, vol. 54, No. 11, Nov. 2006, 12 pages.

(Continued)

*Primary Examiner* — James Pontius
(74) *Attorney, Agent, or Firm* — Hauptman Ham, LLP

(57) ABSTRACT

Disclosed herein is an endoscope. The endoscope includes a light source; an optical fiber having a light entrance portion and a light exit portion such that light containing image information on a site irradiated with light from the light source enters through the light entrance portion and light passing through the optical fiber exits through the light exit portion; and an image acquisition device acquiring the image information, wherein the image acquisition device includes: an image sensor acquiring information of light passing through the optical fiber; a transmission matrix storage unit previously storing a transmission matrix indicating a transmission state of various light components entering the light entrance portion; and an image recovery unit recovering the image information from the information of light acquired by the image sensor through compressed sensing using a sparse representation based on the transmission matrix.

13 Claims, 7 Drawing Sheets

(51) Int. Cl.
*A61B 1/00* (2006.01)
*A61B 1/04* (2006.01)
*A61B 1/06* (2006.01)

(52) U.S. Cl.
CPC ......... *H04N 5/2254* (2013.01); *H04N 5/2256* (2013.01); *H04N 2005/2255* (2013.01)

(56) References Cited

U.S. PATENT DOCUMENTS

| | | | | |
|---|---|---|---|---|
| 7,894,071 | B2* | 2/2011 | Frese | B01L 3/5027 356/440 |
| 8,675,195 | B2* | 3/2014 | Ihlefeld | G01N 15/0205 356/335 |
| 9,007,696 | B2* | 4/2015 | Petersen | A61B 5/0066 359/642 |
| 9,612,186 | B2* | 4/2017 | Wei | G01N 15/0227 |
| 2010/0253949 | A1* | 10/2010 | Adler | A61B 5/0066 356/479 |
| 2011/0304745 | A1* | 12/2011 | Wang | G06T 15/50 348/229.1 |
| 2013/0271592 | A1* | 10/2013 | Piestun | H04N 7/18 348/79 |
| 2014/0240532 | A1* | 8/2014 | Marwah | H04N 5/2621 348/222.1 |
| 2015/0015879 | A1* | 1/2015 | Papadopoulos | G02B 23/26 356/301 |
| 2016/0202165 | A1* | 7/2016 | Wei | G02B 21/0092 356/336 |
| 2016/0258817 | A1* | 9/2016 | Dholakia | G01J 3/0205 |
| 2016/0299033 | A1* | 10/2016 | Choi | G01N 21/59 |
| 2017/0176660 | A1* | 6/2017 | Mirsepassi | G02B 5/021 |

OTHER PUBLICATIONS

Emmanuel J. Candes et al., "Near-Optimal Signal Recovery From Random Projections: Universal Encoding Strategies?", IEEE Transactions on Information Theory, vol. 52, No. 12, Dec. 2006, 20 pages.
[Supportive Materials for Exception to Loss of Novelty] Hwanchol Jang et al., "Speckel suppression via sparse representation for wide-field imaging through turbid media", Optics Express 16619, vol. 22, No. 13, Jun. 30, 2014, 10 pages.
[Supportive Materials for Exception to Loss of Novelty] Antoine Liutkus et al., "Imaging With Nature: Compressive Imaging Using a Multiply Scattering Medium", Scientific Reports, vol. 4:5552, published Jul. 9, 2014, 7 pages.
[Supportive Materials for Exception to Loss of Novelty] Hwanchol Jang et al., "Recent Progress in Computational Imaging Through Turbid Media", The Journal of Korean Institute of Communications and Information Sciences, '14-12 vol. 39A No. 12, 7 pages.
[Supportive Materials for Exception to Loss of Novelty] Hwanchol Jang et al., "Holistic random encoding for imaging through multimode fibers", Optics Express 6705, vol. 23, No. 5, Mar. 9, 2015, 17 pages.

* cited by examiner

ENDOSCOPE

CROSS REFERENCE TO RELATED APPLICATION

This application claims the benefit of Korean Patent Application No. 10-2015-0075285, filed on May 28, 2015, entitled "ENDOSCOPE", which is hereby incorporated by reference in its entirety into this application.

BACKGROUND

1. Technical Field

The present invention relates to an endoscope. More particularly, the present invention relates to an endoscope which can obtain high-quality images without discomfort.

2. Description of the Related Art

An endoscope is used to examine the internal organs and is an indispensable instrument in modern medical environments since it allows the inside of the body to be observed in a minimally invasive or noninvasive manner Such an endoscope is well known in the art and allows the inside of the body to be observed from outside of the body using a light source, an optical fiber, and a camera.

In use of an endoscope, a bundle of optical fibers is inserted into the body. At this time, a patient experiences discomfort such as nausea and foreign body sensations. In order to reduce this discomfort, recently, an endoscope is used when a patient is asleep. However, sleep endoscopy has shortcomings of the burden of anesthesia and side effects resulting therefrom.

Therefore, there is a need for a method of reducing patient discomfort in use of an endoscope by reducing the thickness of a bundle of optical fibers. However, since the amount of transmitted information is reduced with decreasing number of optical fibers, it is impossible to recover an image having sufficient resolution.

BRIEF SUMMARY

Embodiments of the present invention have been conceived to solve such a problem in the art and it is an aspect of the present invention to provide an endoscope which can reduce patient discomfort by minimizing the thickness of optical fibers inserted into his/her body and recover an image having sufficient resolution using a narrower optical fiber, thereby examining the state of the inside of the body accurately.

In accordance with one aspect of the present invention, an endoscope includes; a light source; an optical fiber having a light entrance portion and a light exit portion such that light containing image information on a site irradiated with light from the light source enters through the light entrance portion and light passing through the optical fiber exits through the light exit portion; and an image acquisition device acquiring the image information, wherein the image acquisition device includes: an image sensor acquiring information of light passing through the optical fiber; a transmission matrix storage unit previously storing a transmission matrix indicating a transmission state of various light components entering the light entrance portion; and an image recovery unit recovering the image information from the information of light acquired by the image sensor through compressed sensing using a sparse representation based on the transmission matrix.

The light source may be a coherent light source, preferably a laser. A beam splitter may be disposed between the image acquisition device and the optical fiber, and may allow both a signal beam passing through the optical fiber and a reference beam emitted from the light source to be transmitted to the image sensor.

Turbid media may be provided to the light entrance portion so as to increase a numerical aperture of the light entrance portion, and the turbid media may be obtained by incorporating nanoscale fine particles into a transparent matrix. The fine particles may be formed of ZnO, and the turbid media may be applied to the light entrance portion.

The optical fiber may be a multimode fiber.

The transmission matrix may include thousands of columns, and the columns of the transmission matrix may be calculated at different light incident angles.

A lens system may be provided to a downstream side of the light exit portion.

In accordance with another aspect of the present invention, an endoscope includes: an optical fiber providing a propagation route for light containing image information; and an image acquisition device acquiring the image information from light passing through the optical fiber, wherein the image acquisition device includes: an image sensor acquiring information of light passing through the optical fiber; a transmission matrix storage unit previously storing a transmission matrix indicating a transmission state of light components passing through the optical fiber at different incident angles; and an image recovery unit recovering the image information from the information of light acquired by the image sensor through compressed sensing using a sparse representation based on the transmission matrix.

The present invention can provide an endoscope which can reduce patient discomfort by reducing the thickness of an optical fiber while obtaining image information sufficient to make an accurate diagnosis.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Exemplary embodiments of the present invention will now be described in detail with reference to the accompanying drawings. However, it should be understood that these embodiments are not to be construed in any way as limiting the present invention and that various modifications, changes, alterations, and equivalent embodiments can be made by those skilled in the art without departing from the spirit and scope of the invention.

It should be noted that the accompanying drawings are not to precise scale and may be exaggerated or reduced in optical paths for descriptive convenience and clarity only, a path of light can be shown. However, functions and operations of components can be sufficiently understood.

Figure 1:
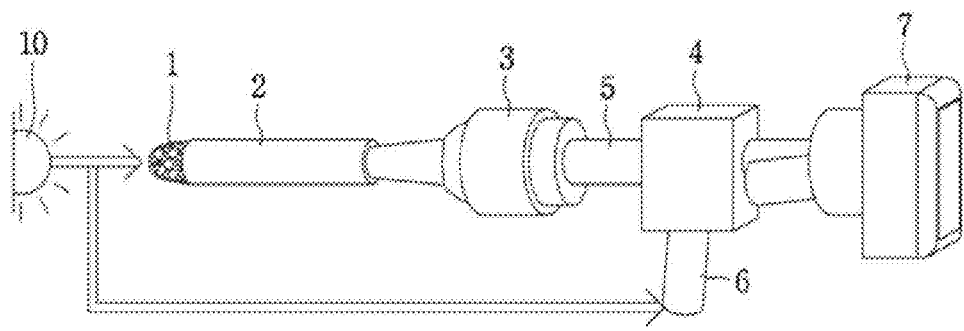
FIG. 1 is a schematic view of an endoscope according to an exemplary embodiment of the present invention.

FIG. 1 is a schematic view of an endoscope according to an exemplary embodiment of the present invention.

Referring to FIG. 1, the endoscope according to the exemplary embodiment of the present invention includes: optical fibers 2, turbid media 1 provided to a light entrance portion of the optical fibers 2, a lens system 3 provided to a light exit portion of the optical fibers 2, a beam splitter 4 provided to an exit portion of the lens system 3, and an image acquisition device 7 provided to an exit side of the beam splitter 4.

One example of the optical fibers may be multimode fibers (MMF). The multimode fibers are fibers in which a plurality of light transmission modes is implemented in optical fibers, and, in this embodiment, the endoscope is operable using a single strand of multimode fibers. Although the present invention does not exclude use of a bundle of two or more optical fiber strands, the endoscope according to the present invention is advantageously operable even with a single strand of multimode fibers. Thus, the endoscope may be realized using optical fibers having a sufficiently small diameter, for example, a diameter of 1 μm or less, whereby user discomfort due to insertion of an instrument into the body can be considerably reduced. The turbid media 1 include fine particles incorporated into a matrix of a transparent resin capable of transmitting light. The turbid media 1 may be applied to the light entrance portion of the optical fibers 2. As the fine particles, nanoscale zinc oxide (ZnO) may be used. An inherent numerical aperture (NA) of the optical fibers can be increased by providing the turbid media 1 to the light entrance portion of the optical fibers. In other words, light is scattered in many directions within the turbid media 1, whereby an angle at which light can enter through the light entrance portion can be widened. For example, light beams being incident at an angle that would not otherwise allow entry into the optical fibers 2 can change travel direction due to the presence of the fine particles to be transmitted into the optical fibers 2. The beam splitter 4 allows acquisition of both a signal beam 5 containing information on an image of the inside of the body and a reference beam 6 from an original light source 10. The endoscope may further include a beam splitter bypassing a portion of light emitted from the light source 10 so as to acquire the reference beam 6. A process of recovering a phase signal by introducing the signal beam and the reference beam into the beam splitter 4 may be referred to as a holographic process. The image acquisition device 7 serves to recover an image signal using an intensity signal of the signal beam and the phase signal of the signal beam, which is obtained by referring to the signal beam and the reference beam.

Next, operations and effects of the endoscope will be described briefly.

After the endoscope is inserted into the body, light emitted from the light source 10 is directed to a certain portion of the body of a subject, and optical information on the portion passes through the turbid media 1 and enters the optical fibers 2. As described above, the turbid media 1 serves to increase a numerical aperture (NA) of the light entrance portion. Optical signals transmitted through the optical fibers 2 pass through the lens system 3 and then enter the beam splitter 4 as the signal beam 5. The beam splitter 4 receives both the signal beam 5 and the reference beam 6. The reference beam 6 may refer to a light beam that is transmitted using another beam splitter or the like after being emitted from the light source 10. The image acquisition device 7 may acquire a phase signal of the signal beam 5 using the reference beam 6 while acquiring an intensity signal of the signal beam 5. The image acquisition device recovers an image using both the intensity signal and the phase signal, thereby obtaining a more accurate image.

Figure 2:
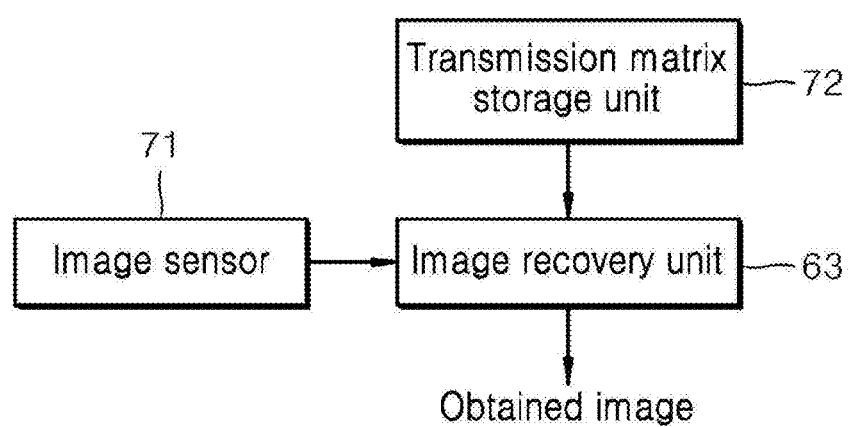
FIG. 2 is a block diagram of an image acquisition device.

FIG. 2 is a block diagram of the image acquisition device.

Referring to FIG. 2, the image acquisition device 7 includes an image sensor 71 acquiring both the signal beam 5 and the reference beam 6 passing through the beam splitter 4, a transmission matrix storage unit 72, and an image recovery unit 73 recovering an actual image of the inside of the body using a transmission matrix stored in the transmission matrix storage unit 72 and an image acquired by the image sensor 71.

Next, the transmission matrix (TM) stored in the transmission matrix storage unit 72 will be described in more detail. The transmission matrix stored in the transmission matrix storage 72 may indicate what image is formed by light incident in many different directions at many different positions toward the light entrance portion and passing through the turbid media 1, the optical fibers 2, the lens system 3, and the beam splitter 4. The transmission matrix may be discerned before market release of the endoscope. Since the transmission matrix may vary depending upon in what manner fine particles are dispersed in the turbid media 1, the transmission matrix may be measured differently for each endoscope. For example, the number of columns of the transmission matrix stored in the transmission matrix storage unit 72 may reach several thousand.

The image recovery unit 73 recovers an image though compressed sensing (CS), wherein the transmission matrix stored in the transmission matrix storage unit 72 and the image acquired by the image sensor 71 are used.

Figure 3:
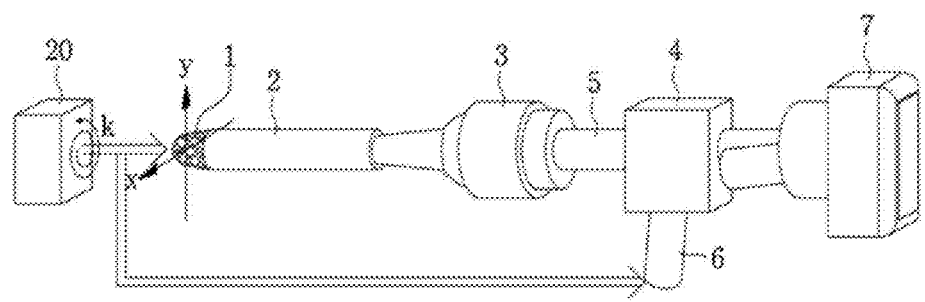
FIG. 3 is a view illustrating a method of measuring a transmission matrix.

FIG. 3 is a view illustrating a method of measuring the transmission matrix.

Referring to FIG. 3, a multi-directional lamp 20 emits light toward the light entrance portion of the endoscope, more precisely the turbid media 1 in various directions at various positions. The multidirectional lamp 20 is capable of emitting laser beams at thousands of angles and thousands of positions in dozens of seconds. By way of example, the transmission matrices may be measured while gradually increasing the distance and angle from the center of the turbid media 1, starting at the center. Each of the transmission matrices may indicate what image is formed in the image sensor 71 by light incident at a certain angle and passing through the turbid media.

Next, the meaning of the transmission matrix will be described with reference to Equation 1:

$$U_o(x, y) = \sum_k A_o(k) P(x, y, k) = I_o(x, y) \exp\{P_o(x, y)\}$$

where $U_o(x,y)$ is an object wave; $A_o(k)$ is an angular spectrum of the object wave (wherein k is a wave vector); and $P(x,y;k)$ is a plane wave having k propagation directions. Thus, the object wave denotes light entering the turbid media 1, and the object wave may be divided into a set of plane waves having k propagation directions.

In Equation 1, $I_o(x,y)$ and $P_o(x,y)$ denote intensity and phase of a light wave at (x,y), respectively. Physically, the object wave may be expressed by intensity information and phase information.

Figure 5:
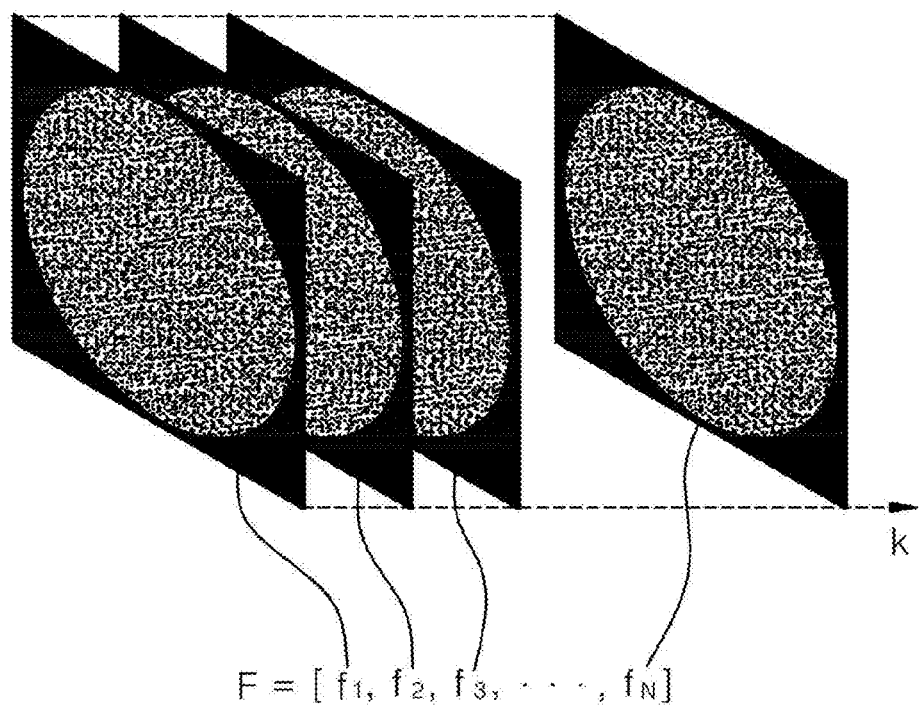
FIG. 5 is a view illustrating the transmission matrix.

When the object wave passes through the turbid media 1 and the optical fibers 2, the object wave is distorted due to scattering properties of the turbid media and transmission properties of the optical fiber. The distorted object wave is acquired by the image acquisition device 7 as the signal beam 5. The distorted object wave is represented by Equation 2:

$$U_r(x, y) = \sum_k A_o(k) F(x, y, k)$$

where $U_r(x,y)$ is a distorted object wave; $A_o(k)$ is an angular spectrum of the object wave; and $F(x,y:k)$ is a response wave after a certain $P(x,y;k)$ (plane wave having k propagation directions) passes through the turbid media and the optical fiber and may denote each column of the transmission matrix. FIG. 5 is a view illustrating the transmission matrix. Referring to FIG. 5, each column of a transmission matrix for plane waves having k propagation directions is designated by f, and the transmission matrix is designated by F and stored in the transmission matrix storage unit 72. Although FIG. 5 shows only intensity information, phase information may also be acquired using a holographic process in which the signal beam is compared with the reference beam. Thus, information on each element of a column of the transmission matrix may be represented by a complex number.

Equation 2 may be expressed in vector notation by Equation 3:

$$r = Fa$$

where r is a vector expression of the distorted object wave; a is a vector expression of an angular spectrum of the object wave; and F is a transmission matrix (wherein each column of the transmission matrix is a vector expression of the response wave). Here, the number of k's may be the number of columns of a transmission matrix acquired using the multidirectional lamp 20.

In Equation 3, since r is information acquired by the image acquisition device and F is information acquired through measurement of the transmission matrix, it is possible to calculate the angular spectrum (a) of the object wave. When the angular spectrum is properly calculated, it is possible to reconstruct the object wave, i.e. an image entering the turbid media 1 according to Equation 1 based on the known $P(x,y;k)$ (plane wave having k propagation directions).

Figure 4:
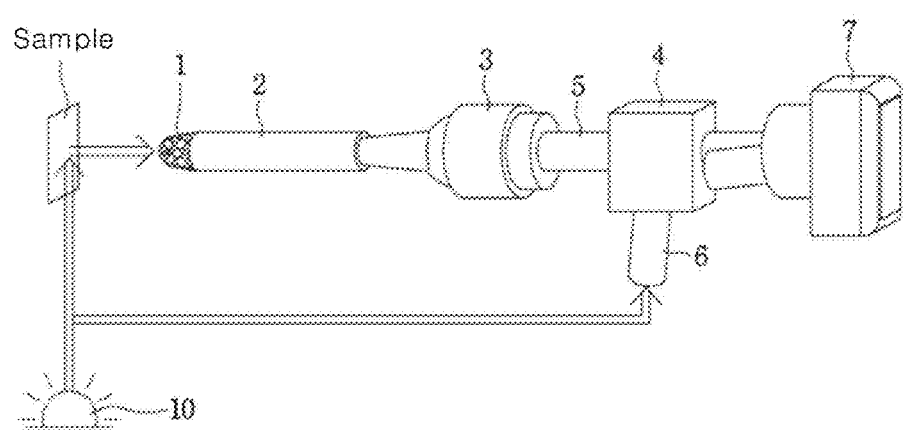
FIG. 4 is a view of the endoscope according to the embodiment of the present invention in use.

FIG. 4 is a view of the endoscope according to the embodiment of the present invention in use.

Referring to FIG. 4, a portion of light emitted from the light source 10 is reflected by a sample and enters the turbid media 1, that is, the light entrance portion of the optical fibers 2. Another portion of light emitted from the light source 10 is bypassed by a separate light division device (not shown) such as a beam splitter and then enters the beam splitter 4 as the reference beam. Since light emitted from the light source 10 is coherent light, it is possible to obtain intensity (amplitude) and phase information from the data acquired by the image sensor. A typical example of the light source 10 may be a laser, preferably an infrared laser, which is harmless to the human body. Use of such a coherent light source can allow image accuracy to be more than doubled as compared with use of an incoherent light source, which is unable to obtain phase information. Thus, as the light source, a coherent light source is preferred. If an incoherent light source is used, the beam splitter 4, the reference beam 6, and a complex number expression for utilizing phase information are unnecessary since the holographic process is not employed.

Although a coherent light source is preferably used to improve image accuracy in this embodiment, the present invention does not exclude use of an incoherent light source.

Figure 6:
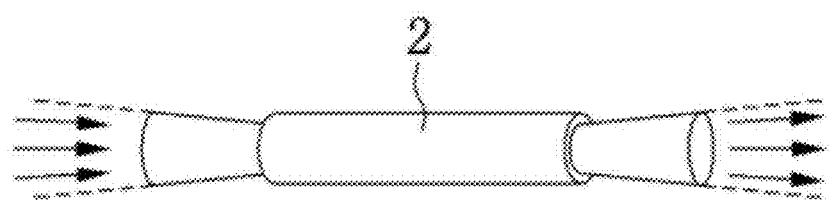
FIGS. 6 and 7 are reference views illustrating an advantage of turbid media.
Figure 7:
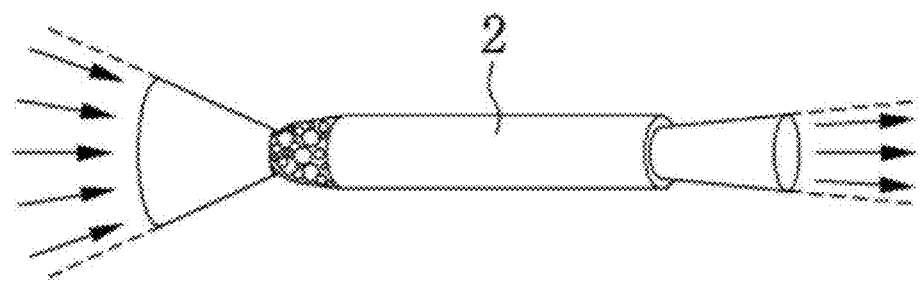

As described above, the turbid media 1 can increase a numerical aperture of the light entrance portion of the optical fibers 2. FIGS. 6 and 7 are reference views illustrating an advantage of the turbid media. The view of FIG. 6 shows the case in which the turbid media is absent, and the view of FIG. 7 shows the case in which the turbid media is provided to the light entrance portion of the optical fiber.

Referring to FIGS. 6 and 7, when the turbid media is provided, information can enter the lens system at an angle that would not otherwise allow entry into the light entrance portion of the optical fiber due to increase in the numerical aperture of the optical fiber. This is because light passing through the turbid media 1 can be scattered by the fine particles to enter the light entrance portion of the optical fiber. Thus, information contained in one transmission mode of the optical fibers 2 may be more mixed information, for a given absolute amount of information contained in one transmission mode of the optical fibers 2. In other words, information that could not enter the lens system without the turbid media 1 can also be transmitted into the optical fiber, whereby a more accurate image can be recovered using the information.

Next, an advantage of the turbid media will be described in more detail. Firstly, output mode signals at the light exit portion of the optical fibers 2 include all input-mode information entering the light entrance portion of the optical fibers 2. When an optical fiber having two or more transmission modes (i.e. multimode fiber (MMF)) is used, it is possible to transmit a larger number of input mode signals. Thus, benefits of the endoscope according to the present invention can be maximized using the multimode fiber. However, it should be understood that a bundle of two or more single mode fibers may be used without departing from the spirit of the invention. Secondly, a linear combination of input mode signals transmitted in one transmission mode is linearly independent from or does not have a correlation with linear combinations of input mode signals transmitted in other transmission modes. Thus, the transmission mode of the optical fiber can be used in the most efficient manner By way of example, in optical fibers having three transmission modes, i.e. first, second, and third transmission modes without turbid media, A, B, and C input-mode signals are transmitted in the transmission modes, respectively. Conversely, when such optical fibers are provided with the turbid media 1, D and E input-mode signals that could not otherwise enter the lens system can be input to the optical fibers and each of A, B, C, D, and E input-mode signals can be transmitted through the optical fibers in any one of the first, second, and third transmission modes, each of which is present in the form of a mixture of at least two of transmission modes for A, B, C, D, and E input-mode signals.

From the above description, advantages of the endoscope including the turbid media according to the present invention will become apparent.

Next, a process of finding an angular spectrum of the object wave will be described with reference to Equation 3. Equation 3 is an underdetermined system and a solution thereof may be found through an optimization process. In one embodiment, the solution of Equation 3 is found by compressed sensing using a sparse representation.

In order to successfully perform compressed sensing using a sparse representation, two requirements must be satisfied.

Firstly, the angular spectrum (a) of the object wave in Equation 3 must be a compressible signal. Herein, the term "compressible" means that the angular spectrum (a) of the object wave has a small number of nonzero elements. Images of the natural world including an image of the inside of the body to be observed using the endoscope of the invention can be expressed by a small number of elements in a wavelet domain. Further, it is known that when an image can be expressed by a small number of elements even in an orthogonal signal base other than a wavelet domain, signals of the image are compressible.

Specifically, this is known through: M. Aharon, M. Elad, and A. Bruckstein, "K-SVD: an algorithm for designing overcomplete dictionaries for sparse representation," IEEE Trans. Signal processing. 54, 4311-4322 (2006); and E. J. Candes and T. Tao, "Near-optimal signal recovery from random projections: universal encoding strategies," IEEE Trans. Inf. Theory. 52, 5406-5425 (2006).

Secondly, the transmission matrix F in Equation 3 must be incoherent. In compressed sensing, the transmission matrix F is obtained by measuring characteristics of the turbid media 1 and the optical fibers 2 and thus may be referred to as a measurement matrix. When columns of the transmission matrix have low cross-correlation with one another, the transmission matrix can be said to be incoherent. Each of the columns of the transmission matrix is a measurement value of each of light components emitted in different directions by the multidirectional lamp 20. Since the measurement value changes randomly when the light beams pass though the turbid media 1, it can be ensured that the transmission matrix is incoherent. Even when the turbid media 1 are not provided, incoherence of the transmission matrix can be obtained at a certain level due to difference between transmission modes of the optical fibers 2. Thus, when the turbid media 1 are not used, it is possible to employ compressed sensing using a sparse representation. However, it is more desirable, in order to maximize effects of compressed sensing, that the turbid media 1 be used.

Next, a difference in incoherence of the transmission matrix between the case in which the turbid media 1 are used and the case in which the turbid media are not used will be described with reference to the accompanying drawings.

Figure 8:
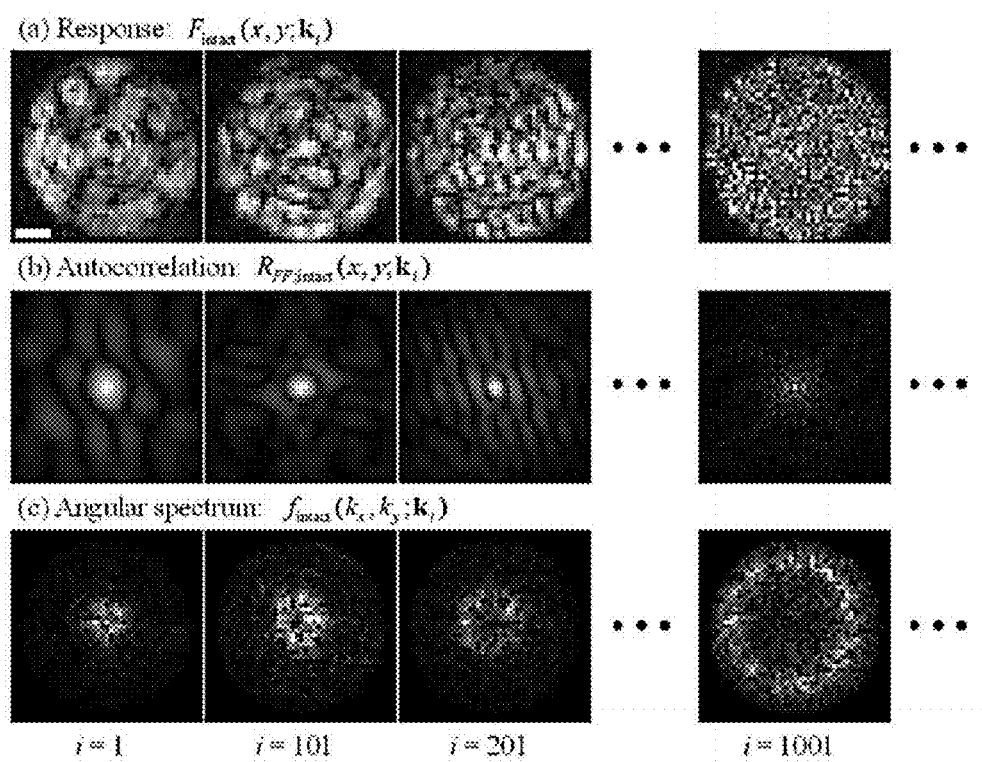
FIG. 8 shows the case in which the turbid media are not used.
Figure 9:
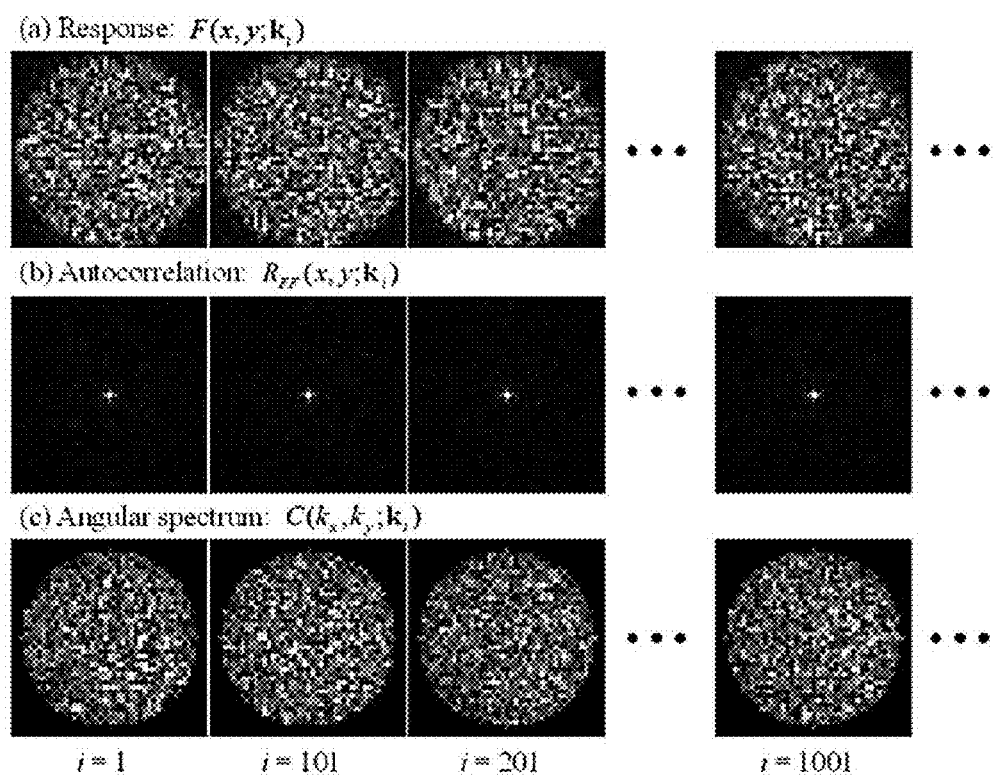
FIG. 9 shows the case in which the turbid media are used, wherein (a) is a column of a transmission matrix (for each serial number (i)) calculated for light emitted from a multi-directional lamp, (b) is an autocorrelation of the column of the transmission matrix, and (c) is an angular spectrum of the column of the transmission matrix.

FIG. 8 shows the case in which the turbid media are not used (with the optical fibers intact) and FIG. 9 shows the case in which the turbid media are used (or coated). Here, (a) is a column of a transmission matrix (for each serial number (i)) calculated for light emitted from the multi-directional lamp 20; (b) is an autocorrelation of the column of the transmission matrix; and (c) is an angular spectrum of the column of the transmission matrix.

Referring to (a) of FIGS. 8 and 9, it can be seen that the columns of the transmission matrix have relatively high irregularity when the turbid media are used. Referring to (b) of FIGS. 8 and 9, it can be seen that, when the turbid media are provided, the columns exhibit much higher autocorrelation and are thus gathered around the center. In addition, referring to (c) of FIGS. 8 and 9, it can be seen that the angular spectrums are evenly spread over the entire area.

Therefore, when the turbid media are provided, compressed sensing using a sparse representation is preferably used. Although use of the turbid media is more preferable in compressed sensing using a sparse representation, it should be noted that the present invention is not limited thereto and the optical fibers may be used without the turbid media. However, from the above description, it will be apparent that use of the turbid media is considerably desirable.

From the above description, it can be confirmed that an optimal solution of the underdetermined system represented by Equation 3 may be found by compressed sensing using a sparse representation. A method of finding the optimal solution through compressed sensing using a sparse representation is represented by Equation 4:

$$\hat{a}_{SR} = \underset{a}{\operatorname{argmin}} \|\Psi^* a\|_1 \text{ subject to } r = Fa$$

where $\Psi$ is a sparsifying basis estimated such that the angular spectrum (a) of the object wave has a small number of nonzero elements. $(.)^*$ is a conjugate transpose of the matrix. $\|.\|_1$ is an L1-norm and denotes the sum of absolute values of vector elements.

An optimal solution of Equation 4 may be found by simplex methods, steepest decent methods, or second derivative methods. By way of example, the optimal solution may be found by an L1-norm minimizing method disclosed in Korean Patent No. 10-1423964 of the present applicant.

When the angular spectrum of the object wave is calculated according to Equation 4, an image can be recovered by the method described in Equation 3.

Next, a specific embodiment of the endoscope and results of testing according to the embodiment will be described with reference to the above features.

As the optical fibers 2, a single strand of multimode fibers (MMF) (M14L01, Thorlabs Optics, numerical aperture: 0.22, length: 1 m) was used. The turbid media obtained by incorporating nanoparticles of nanoscale zinc oxide (ZnO) into a transparent resin were placed at the light entrance portion of the turbid media. Measurement was performed 4,000 times while irradiating an observation object with laser beams at 633 nm using the multidirectional lamp 20, the direction of which is adjusted using a galvanometer, thereby obtaining a transmission matrix. Here, a sample similar to a USAF target was used as the object.

Four cases were tested: the cases in which compressed sensing using a sparse representation or a pseudo inversion method (PINV) was employed in the presence or absence of the turbid media. Specifically, FIG. 10 shows respective images recovered by a pseudo inversion method (PINV) and compressed sensing using a sparse representation (SR) without the turbid media, and FIG. 11 shows respective images recovered by a pseudo inversion (PINV) method and compressed sensing using a sparse representation (SR), respectively with the turbid media provided.

Figure 10:
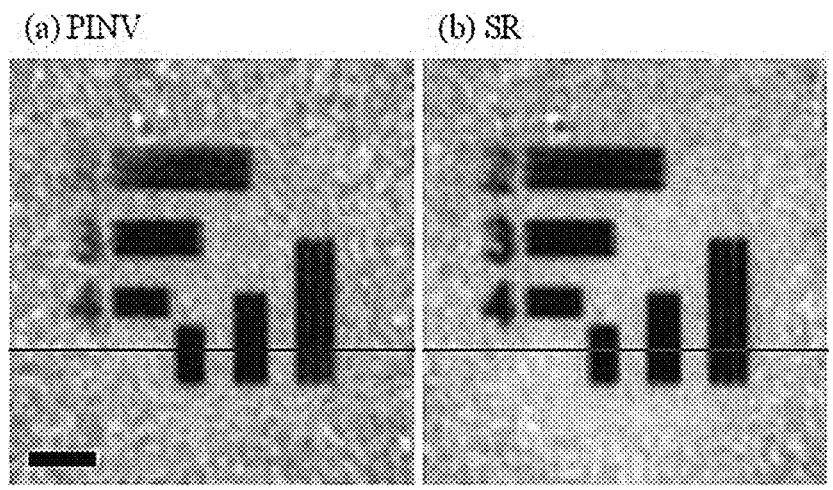
FIG. 10 shows respective images recovered by a pseudo inversion method and compressed sensing using a sparse representation without the turbid media.
Figure 11:
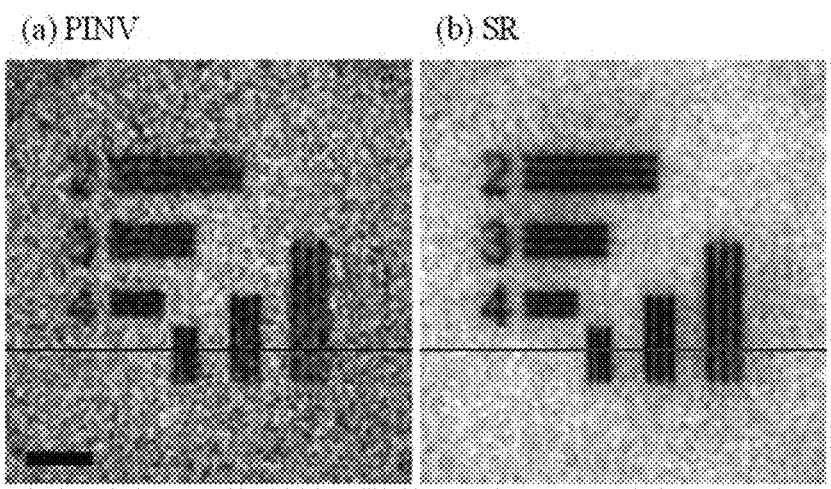
FIG. 11 shows respective images recovered by a pseudo inversion method and compressed sensing using a sparse representation with the turbid media provided.

Referring to FIGS. 10 and 11, it can be seen that the images recovered using the turbid media had further improved quality and the images recovered by compressed sensing using a sparse representation had further improved quality.

According to the present invention, it is possible to considerably reduce a diameter of a portion of an endoscope which is inserted into the body, thereby eliminating patient discomfort. In addition, the embodiments of the present invention allow a recovered image to have high resolution and are thus expected to have high applicability to endoscopes. Further, besides endoscopes, the embodiments of the present invention can be advantageously applied to any instrument for observing the inside of a site not visible from outside by inserting an elongated article, such as an optical fiber, into the site.

Although the present invention has been described with reference to some embodiments, it should be understood that the foregoing embodiments are provided for illustration only and are not to be construed in any way as limiting the present invention, and that various modifications, changes, alterations, and equivalent embodiments can be made by those skilled in the art without departing from the spirit and scope of the invention.

What is claimed is:

1. An endoscope comprising;
    a light source;
    an optical fiber having a light entrance portion and a light exit portion such that light containing image information on a site irradiated with light from the light source enters through the light entrance portion and light passing through the optical fiber exits through the light exit portion; and
    an image acquisition device acquiring the image information,
    wherein the image acquisition device comprises:
    an image sensor acquiring information of light passing through the optical fiber;
    a memory configured to store a transmission matrix indicating a transmission state of various light components entering the light entrance portion; and
    a processor configured to recovery the image information from the information of light acquired by the image sensor through compressed sensing using a sparse representation based on the transmission matrix.

2. The endoscope according to claim 1, wherein the light source is a coherent light source.

3. The endoscope according to claim 2, wherein the light source is a laser.

4. The endoscope according to claim 1, wherein a beam splitter is disposed between the image acquisition device and the optical fiber, and allows both a signal beam passing through the optical fiber and a reference beam emitted from the light source to be transmitted to the image sensor.

5. The endoscope according to claim 1, wherein turbid media are provided to the light entrance portion so as to increase a numerical aperture of the light entrance portion.

6. The endoscope according to claim 5, wherein the turbid media are obtained by incorporating nanoscale fine particles into a transparent matrix.

7. The endoscope according to claim 6, wherein the fine particles are formed of ZnO.

8. The endoscope according to claim 5, wherein the turbid media are applied to the light entrance portion.

9. The endoscope according to claim 1, wherein the optical fiber is a multimode fiber.

10. The endoscope according to claim 1, wherein the transmission matrix comprises thousands of columns.

11. The endoscope according to claim 1, wherein the columns of the transmission matrix are calculated at different light incident angles.

12. The endoscope according to claim 1, wherein a lens system is provided to a downstream side of the light exit portion.

13. An endoscope comprising:
    an optical fiber providing a propagation route for light containing image information; and
    an image acquisition device acquiring the image information from light passing through the optical fiber,
    wherein the image acquisition device comprises:
    an image sensor acquiring information of light passing through the optical fiber;
    a memory configured to store a transmission matrix indicating a transmission state of light components passing through the optical fiber at different incident angles; and
    a processor configured to recovery the image information from the information of light acquired by the image sensor through compressed sensing using a sparse representation based on the transmission matrix.

* * * * *